United States Patent [19]

Kass

[11] Patent Number: 4,615,878

[45] Date of Patent: * Oct. 7, 1986

[54] METACHROMATIC DYE SORPTION MEANS FOR DIFFERENTIAL DETERMINATION OF SUB-POPULATIONS OF LYMPHOCYTES

[76] Inventor: Lawrence Kass, 1939 Ridge Rd., Hinckley, Ohio 44233

[*] Notice: The portion of the term of this patent subsequent to Aug. 23, 2000 has been disclaimed.

[21] Appl. No.: 604,869

[22] Filed: Apr. 27, 1984

Related U.S. Application Data

[63] Continuation-in-part of Ser. No. 129,680, Mar. 12, 1980, Pat. No. 4,581,223, and a continuation-in-part of Ser. No. 242,662, Mar. 11, 1981, Pat. No. 4,400,370, and a continuation-in-part of Ser. No. 356,578, Mar. 9, 1982, Pat. No. 4,500,509.

[51] Int. Cl.$^4$ .................. G01N 1/30; G01N 33/49; G01N 33/52
[52] U.S. Cl. .................. 424/3; 424/7.1; 436/63
[58] Field of Search .......... 424/3, 7.1; 8/644, 657; 436/63; 250/461.2

[56] References Cited

U.S. PATENT DOCUMENTS

| | | | |
|---|---|---|---|
| 2,126,852 | 8/1938 | Wolff | 546/176 |
| 3,617,185 | 11/1971 | Drautz | 8/527 |
| 4,146,604 | 3/1979 | Kleinerman | 436/800 X |
| 4,390,518 | 6/1983 | Fischer | 424/3 |
| 4,400,370 | 8/1983 | Kass | 424/3 |
| 4,492,752 | 1/1985 | Hoffman | 424/3 |
| 4,500,509 | 2/1985 | Kass | 424/7.1 X |
| 4,581,223 | 4/1986 | Kass | 424/3 |

OTHER PUBLICATIONS

Lanier et al. (1983), J. of Immunology 131(4): 1789–1796.

Primary Examiner—Christine M. Nucker
Assistant Examiner—Cynthia Lee Foulke
Attorney, Agent, or Firm—Richard G. Smith

[57] ABSTRACT

Differentiation, identification and enumeration of sub-populations of lymphocytes including B-cells and T-cells can now be further discriminated into their sub-populations by means of basic orange 21 as a supravital stain to provide distinctive morphologic differences between B-cells, T-suppressor cells, T-helper cells and natural killer (NK) cells without resorting to the use of individual monoclonal antibodies for differentiation of each of the above.

The differentiation, identification and enumeration of the foregoing cells can be accomplished by means of both white light absorbance and fluorescence measurements, singly or in sequential combinations.

5 Claims, 1 Drawing Figure

FIG. I

CELL CLASSIFICATION

ABSORBANCE | FLUORESCENCE

B CELL

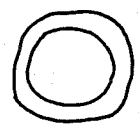 PALE YELLOW NUCLEUS AND CYTOPLASM

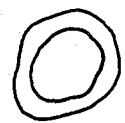 PALE GREEN NUCLEUS AND CYTOPLASM

T - HELPER

 DARK YELLOW NUCLEUS AND CYTOPLASM, PROMINENT NUCLEAR CHROMATIN AGGREGATES

 BLUE GREEN NUCLEUS AND CYTOPLASM

T - SUPPRESSOR

 DARK YELLOW NUCLEUS AND CYTOPLASM, PROMINENT NUCLEAR CHROMATIN AGGREGATES, SMALL RED GRANULES

 BLUE GREEN NUCLEUS AND CYTOPLASM, SMALL YELLOW GRANULES

NK OR NATURAL KILLER

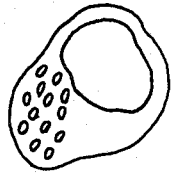 LARGE CELL, YELLOW NUCLEUS AND CYTOPLASM, LARGE RED GRANULES

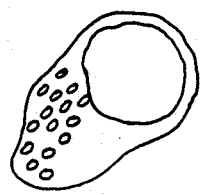 GREEN NUCLEUS AND CYTOPLASM, LARGE YELLOW GRANULES

METACHROMATIC DYE SORPTION MEANS FOR DIFFERENTIAL DETERMINATION OF SUB-POPULATIONS OF LYMPHOCYTES

CROSS REFERENCE TO RELATED APPLICATIONS

This application is a continuation-in-part of my co-pending application, U.S. Ser. No. 129,680, filed Mar. 12, 1980 now U.S. Pat. No. 4,581,223, herein called the parent; and continuation-in-part applications thereof, namely; U.S. Ser. No. 242,662, filed Mar. 11, 1981 now U.S. Pat. No. 4,400,370; and a continuation-in-part of pending U.S. Ser. No. 356,578, filed Mar. 9, 1982, now U.S. Pat. No. 4,500,509.

BACKGROUND OF THE INVENTION

1. Field of the Invention

The present invention is an unexpected further discovery of the unique qualities of basic orange 21, a textile dye, originally disclosed in the above parent application, U.S. Ser. No. 129,680, to identify the principal human blood leukocytes.

Further detailed studies have established that this same dye can also identify and provide means for differentiation and enumeration of sub-populations of T-lymphocytes, including T-helper cells, T-suppressor cells, and natural killer (NK) cells (which latter cells are not strictly T-cells in the same way as the first two mentioned T-helper and T-suppressor cells are).

The ability to use a supravital dye, rather than monoclonal antibodies, to distinguish the various lymphocytes advances in the art relating to immunology, investigation of the immune system and its disorders, including the assessment of the body's ability to reject malignancies and tolerate organ transplants.

The present discovery records a single supravital dye stain which provides the means to identify certain lymphocyte sub-populations by both absorbance (as in a light microscope) as well as using fluorescence emissions stimulated in the basic orange 21 supravitally stained human blood containing biopsy specimens. Automated instrumentation utilizing the advances in discrimination are now under development.

2. Description of the Prior Art

A review of the state of the art indicates it is almost universal practice, before staining (which presently uses a plurality of chemical differing dyestuffs in admixture) to employ a fixative procedure which may require up to an half hour treatment before the biological specimen is subjected to dye stain. Fixatives are generally preservatives and denaturants that often interfere with the sensitivity of the dye sorption. Illustratively, fixatives include formaldehyde both as liquid and vapor, absolute alcohols (methyl), picroformal, etc. Very often living cells do not stain using vital dyes and fixatives have been essential to staining the specimens. Cytochemistry includes considerable information on techniques developed to assure reproducible staining of blood cells. Many essential additives are normally unstable and deteriorate rapidly, thus making cellular identification difficult and in some instances unreliable. Dr. Thomas E. Necheles has observed in relation to leukocyte analysis that this "system has undergone little or no change in fifty years".

Dye staining does serve, however, as a means of discernment of otherwise undiscernable detail of conferring a color reaction on cells and their stainable components; metabolical, functional or pathological.

United States hospitals began leukocyte counting in the early 1900's, using the count as indicia as to whether emergency surgery was necessary, for example. In the U.S. alone, more than half a million differential counts are performed every day, most of them by manual methods. It is important that total white cell counts and differential cell counts be performed and reported without delay. Time is of essence and providing required analysis more rapidly is a desideratum.

The value of leukocyte counting having been established, the demand for rapid blood analysis has developed so that beginning about 1950 with the work of Mellors, R. C., Glassman, A., and Papanicolaou, G.N. "CANCER" 5: 458–468, 1952. development of automated differential leukocyte counting instrumentation means had developed into a plurality of instruments by 1980. The CYDAK unit was early used to investigate the feasability of blood cell classification which pointed up the importance of specialized staining procedures and features were extracted from optical density histograms of each cell image. The procedure established that cells could be differentiated into four of the five classes of leukocytes, namely; neutrophils, eosinophils, lymphocytes and monocytes. Young, L.T. AUTOMATED LEUKOCYTE RECOGNITION, a Ph.D. Thesis, M.I.T., 1969. published results on an automated classification of five cell classes and Bacus, J. W. in 1971 (AN AUTOMATED CLASSIFICATION OF THE PERIPHERAL BLOOD LEUKOCYTES BY MEANS OF DIGITAL IMAGE PROCESSING—A Ph.D. Thesis—University of Illinois Medical Center extended the differentiation.

However, it is understood that automated differential systems presently rely upon multiple dye usage and dye degradation systems or indirect fluorescent measurement using fluorescent dyes.

In the prior art staining of blood it has been observed that it is practice to use two or more stains in combination (Romanowski, Giemsa and Wright stains). These methods are difficult in practice to provide quality control. The methods require standardization in preparation of each dye stain component as well as in the method of specimen staining. In development of successful automated leukocyte counters, reproducibility of staining is even more important to verifiable analysis.

LARC stainer (used in commercial automated differential leukocyte counter) is reported (Megla, G. K., Acta Cytologica 17:3-14, 1973) to be a mixture of some thiazine dyes, eosin Y and $2^1$, $4^1$, $5^1$ tribromofluorescein (P. N. Marshall Romanowski Staining: State of the Art and "IDEAL TECHNIQUES: *IN DIFFERENTIAL LEUKOCYTE COUNTING*", edited by Koepke, J. A. CAP, 1971, pp. 205–216.). Present art stains most often are in fixative alcoholic solutions and employ two or more stains in combination. Accurate analysis of vital blood staining is made most difficult. With the difficulty presented in the controlled oxidation of methylene blue essential to Romanowski stains, for example, the problems of quality control of the added ten individually different dye stains as are used in combination become awesome.

It has been recognized in the art that the widespread standardization and adoption of a limited number of stains would ensure greater accuracy and reproducibility in cytological studies. Serious introduction of artifacts have been observed by use of fixatives and cause difficulty in interpretation and misinterpretation in leukocyte differentiation and enumeration. pH adjustments and heavy metal cations have been reported to prevent cytochemical tests from working in the expected manner. Some dyes, particularly azo dyes, are noted to demonstrate non-specific precipitation around cells; other degenerative changes in fixed blood samples include vacuoles, clover-leafing of nuclei, distortion cell shapes and smudges and interference with ideal staining. The importance of performing differential counts on as near living cells in the shortest possible time in order to obtain optimally useful and valuable blood cell analyses has been recognized. Alcoholic dye solutions interfere with supravital staining. So far as is know, freshly prepared water soluble stains exhibit a minimum denaturant effect upon supravital blood during examination. All dyestuffs are more or less toxic to the blood cells, but some are more so than others. It is material that the cells under examination remain living as long as possible. Rapidity of staining obviously shortens the exposure time, thus allowing greater opportunity to examine leukocyte cells before all vitality is lost. Automated differential leukocyte counting in less minutes is sought for.

Studies and review of the prior art of performing microscopic blood analyses and disease diagnosis has indicated it is not unusual for pathologists to warm the dye and the blood specimen to body temperatures (about 37° C.) before contact. Dr. Sabin had a "warm box" to insure temperature control (BULLETIN OF JOHNS HOPKINS U. Vol. XXXIV, No. 391, September 1923, pages 277-278).

It has also been noted that some dyes used in the prior art are quite temperature sensitive. The literature reports that cresylecht violet is not an operative stain above 30° C. It is considered important for the purpose of this method as disclosed herein that the dyestuff be useful to stain leukocytes at temperatures as high as 37° C. and no difficulty has been observed with the select dyes to temperatures of about 40° C.

In the parent application a relatively small number of metachromatic dyestuffs are disclosed as useful in identification of one or more species of leukocyte. Identification and differentiation was specifically related to polymophonuclear leukocytes (neutrophils), basophils, lymphocytes generally, and monocytes. A uniting commonality observed was that all of the dyes found to be operative for the purposes of the parent application metachromatically stained monocytes differentially from others in the above group.

The unusual qualities of the dye basic orange 21 (CI #480352) were observed in relation to the eosinophils, basophils, and monocytes, but as the B-cells are few in number they were initially overlooked. It was intially observed in the parent case that optical differentiation between mature and immature neutrophils appeared potential in that the mature granules were different in chroma from the immature granules which were more red and orange in comparison. As this group; including myeloblasts, promyelocytes, myelocytes, metamylocytes and bands are not always present in all blood specimens or present in significant numbers as is often the case with T-lymphocytes (or T-cells) and B-lymphocytes (or B-cells) they were not then all specifically identified as being metachromatically and differentially stained by basic orange 21.

Subsequent to completion of the work supportive of the parent application, continuing research on the use of this unique dye in similar blood donor studies established that it was reproducibly possible, using this selected basic cationic dye of the methine, polymethine and quinoline class to distinguish through metachromatic response certain lymphocytes. It is also possible further to identify at least ten recognized granulocytes and lymphocytic cells established in the art to be of vital interest to the health sciences.

Further, this differentiation was immediate, it required no complex biochemistry or arduous pre-treatment of the blood specimens. Additionally, it was noted the dye exhibited minimum toxicity.

Microspectrophotometric measurements were made with an aperture small enough to measure the color in the granules of supravitally stained leukocyte granulocytic cells. No other parts of the cell which entered into the measurements to any extent were found to provide extinction coefficients of the colors of the different leukocyte species. These species were consistently different and were often of an order of differences in hue, value or chroma of the order of 50 nanometers. These were recognizable peaks, consistent over many cells. It is understood that differences of the order of 5 nm are significant in microspectrophotometric measurements if the differences are consistent and reproducible.

Among the immature granulocytic cells immediately identifiable and distinguishable one from the other are myeloblasts and cells of the myeloid series, namely; promyelocytes, myelocytes and metamyelocytes. These are believed to be and are generally understood to be precursors of the polymorphonuclear leukocytes or neutrophils, which are also stained metachromatically so as to be readily and easily distinguished, identified and enumerated by the supravital blood analyses made possible by the advances disclosed herein.

As disclosed in the parent application, it is also practical at the same time to distinguish neutrophils, eosinophils, basophils, lymphocytes and monocytes from each other and from the foregoing precursors should they all be present in a specific blood sample under microspectrophotometric analyses.

Additionally, it has also been found that this unique dye provides an optically different pattern of color as well as a different density of each color of granule in band cells. Thus, this quality of leukocyte cell can also be uniquely separated by optical differentiation from the other immature cells identified above. The differentiations in color, color arrangement and color density are also of such a degree of magnitude of difference that human counting of all the above individually named cells can be done by a competent operator. Evidence available also indicates automatic differential counting equipment will develop based upon and to be accommodated by differences due to the presence or absence of color and the physical patterns established in the nucleus and by the relative number, size, arrangement or pattern and hue, value and chroma (color) and color density due to the number of granules in the cytoplasm.

Almost unbelieveably, but also demonstrated in the basic research thus far completed, is the further ability to differentiate B-lymphocytes or B-cells from T-lymphocytes or T-cells. Again, it is possible to specularly identify each of these important lymphocytes, one from the other, qualitatively and quantitatively using the same dyestuff in the same supravital, fixative free analysis as well as to distinguish and enumerate the T-cells and B-cells from each of the foregoing individual immature and mature cells including bands.

Further discovery of the capacity of basic orange 21 to differentiate additionally myeloblasts and blood cells of the myeloid series as well as bands and T-lymphocytes and B-lymphocytes extends the original potential field of usefulness of the dye unexpectedly beyond the capacity recognized in the parent application.

Supravital blood specimen fractions of fluids associated with healthy tissue or tissue suspected of abnormality such as plasma, lymph, serum, etc., containing one or more of the above cells after metachromatic staining may be examined to differentiate each species of cell indicated above permitting enumeration and comparative study.

The present advance in the art, coupled with the parent disclosure establishes unparalleled advance in hematology, cytology and immunology and the ability to plan and conduct researches in an unlimited area of human health. Need for costly reactants, invaluable research time and more accurate data assembly have been thereby measurably advanced.

The parent application reports a study of eighteen carbocyanine dyes, only one of which displayed similar metachromatic staining. Carocyanines, quinoids and methine and polymethine dyes are often very similar chemical structure.

Detailed and specific study of the structure of basic orange 21 (Color Index 48035) disclosed in U.S. Pat. No. 2,126,852 led to testing of basic orange 22 (Color Index #48040). A study of the two chemical structures led to astonishing results. Basic orange 22, does not exhibit metachromasia to any practical level of usefulness for the purposes herein.

Prior art indicated that it was not unusual in supravital analyses to employ three concentrations of dye in three preparations of slides in such analyses as are an essential check on results. With basic orange 21, the color differentials are so separated and the colors so exceptionally vivid that one can readily distinguish primary from secondary granules, instantly, with one dye and one slide.

In the absence of fixatives, the basic dye of this invention is sorbed metachromatically so that each one class, type or species of leukocyte, lymphocyte or granulocyte reflects a characteristic light spectra or color different from every other class, type or species of blast, myeloid cells, leukocyte or ganulocyte present in the sample. The strikingly vivid metachromasia of the single orange dyestuff of this invention has been, so far as presently know, unique and remarkable. Each species of the series including myeloblasts, promyelocytes, myelocytes, metamyelocytes, bands, neutrophils, eosinophils, basophils, B-lymphocytes, T-lymphocytes and monocytes so sorbs the single metachromatic stain as to reflect a distinguishing light spectra or color in the visible light range. Combinations of the dye of this invention with others as suggested in the parent application may be useful in some leukocytes analyses as indicated therein.

An apparent third level of difficulty involving differentiation of neutrophils into immature and mature forms and the division of lymphocytes into normal and reactive types was originally recognized and mentioned in my parent application U.S. Ser. No. 129,680 of Mar. 12, 1980 now U.S. Pat. No. 4,581,223. So far as is presently known this disclosure provides the only method of simply differentiating by means of one single pure dyestuff the blasts, myeloid series, bands, polymorphonuclear leukocytes (neutrophils), eosinophils, basophils, B-cells and T-cells as well as monocytes and platelets with a single dye and single specimen fraction.

The present state of the art in automated differential leukocyte counters is in the development stage insofar as the use of white light and a simple aqueous dye is concerned. Manual differentials with preliminary complexity appear to be principally relied upon. Automated differential counters are said to be of two general classes of groups: 1. pattern recognition systems and 2. cytochemical differentiation systems. It is understood that staining methods of the prior art have been used with greater or less success and machine operations can monitor the operation on a cell-by-cell basis. Usually only 100 cell differential counts are made. Cytochemical systems, while precise, have yet to develop satisfactory calibrators and require highly qualified operators.

In a brief survey of the fluorescent methods of the prior art, the following points are of record. 1. At least two light sources are essential including violet and ultraviolet light. 2. A third light source appears needed as well. 3. The system is understood to require a plurality of fluorescent dye stains to identify and differentiate the species of leukocyte. 4. The system requires alcohol-fixed blood smears. 5. Required staining time is of the order of ten minutes and rinsing for one minute followed by drying. 6. There appears to be a decreasing order of fluorescence intensity from (a) eosinophils to (b) neutrophils to (c) monocyte to (d) lymphocytes. (Basophil identification is not reported.) 7. In a flow tube system, the blood cells are fixed with formaldehyde and stained with three different stains. 8. Detected leukocyte fluorescences are differentially counted and classified by means of ratios of fluorescent light. 9. One patentee discloses identification of only four of the five leukocyte species. 10. Three fluorescent dyestuffs are specified which must be combined to produce a "single dye" composition which combination of dyes appears essential to the operation or method, not merely advantageous.

The methods disclosed herein are based on a supravital technique. There is possible a continuous monitoring system in hospital diagnosis and treatment where continuous critical white blood cell observation directly on the patient would be a desired end, such is within the potential here.

The term supravital stain and supravital staining does not preclude the possibility of continuous perfusion through a shunt circuit from the blood vessels of living organisms and continuous monitoring of all possible blood cells as they are passed through a specialized by-pass tube for observation and count.

It is known that most dyes are toxic when used under supravital conditions. Basic orange 21 is the least toxic dyestuff noted to date for the purposes herein. It has been noted in the prior art that white cells are easily damaged if all red cells are stained in a warm box at 37° C. Prior art has also noted that if a group of cells are stimulated or damaged, reaction to dyes may be markedly changed. It is not unusual that some prior art dye staining requires relatively long periods, on the order of an half hour to obtain maximum dye intensity. The lymphocyte and leukocyte dye of this invention stain almost instanteously, no time is required after contact. Thus the cells are subjected to examination in the least denatured form presently known. Excessive times of exposure may interfere with the sharp initial differentiation.

Based on limitations inherent in panoptically stained specimens, over the past several decades a number of cytochemical tests have been devised to more precisely distinguish one type of blood cell from another. In general, these tests are designed to detect increased amount of one type of substance in a particular cell compared to another, or to detect a substance(s) within a characteristic cellular organelle in one cell compared to another.

For example, activity of non-specific esterase is unusually high in monocytes and this activity appears to be particularly sensitive to inhibition by sodium fluoride. Likewise, identification of granulocytic cells depend for the most part upon demonstration of properties of lysosomes. For these purposes, detection of myeloperoxidase and specific esterase activites have been useful as cytochemical tests. Lysosomal granules of eosinophils contain myeloperoxidase that is resistant to inhibition by sodium cyanide, and granules of basophils stain metachromatically with a variety of dyes, due in part to their high content of cationic substances like heparin.

Extension of studies with basic orange 21 have shown a surprising development over the parent application hereof. It was initially noted that basic orange 21 had some unusual qualities and this as well as the two prior continuations-in-part verifies the initial observations therein noted.

All blood cells appear to originate from undifferentiated stem cells called mesenchymal cells. Immediate descendants of the stem cells are called blasts, and the specific myeloblasts are understood to be progenitors of the leukocytes differentiated and made identifiable and enumeratable by their supravital analyses when exposed to basic orange 21 in a fixative free aqueous environment. Myeloblasts are identified herein by the absence of granules of lysosomes which characteristically identify the three descendant cells of the myeloid series by their meachromatic color sorbtion. The three descendent cells, namely; promyelocytes, myelocytes and metamyelocyte are each separately identified by metachromatic and differential color and color distribution.

Promyelocytes are readily identified by the following manual or automatic observations. They are generally largest in size of the myeloid series. The oval nucleus is not stained by basic orange 21 and is relatively a large part of the total granulocytic cell. The cytoplasm thereof is closely packed with larger numbers of relatively small primary granules of an orange-red color and a few scattered violet granules may also be observed generally distributed amongst the mass of orange-red granules.

Myelocytes also possess a non-stained ovate nucleus of slightly reduce area (volume). The outstanding distinguishing fact is the definite development in the myelocyte of larger secondary yellow granules in a generally thickening crescent of the immature myelocyte cell.

One can observe that myelocytes are distinguished from promyelocytes by the noticeable isolated component of developing secondary larger yellow granules.

Metamyelocytes also have a non-stained nucleus which begins to exhibit developing lobular pattern as distinct from the priorly described ovate form of the first cell in the myeloid series. The diminishing mass of smaller, primary, orange-red granules now becomes a minor proportionate area of the total area of the observed cytoplasm of the cell. Larger secondary yellow granules appears to displace a significant central portion of the previously ovate unstained nuclear, which defines the change intended by the verbal express—from ovate to lobular—.

Bands are progressively distinctive and have been set apart from the first three cells described showing metachromatic staining of the granules and which are members of the myeloid series.

So far as presently known, bands have not been heretofore distinguished from all other leukocytes by the metachromasia of any dye.

Bands are distinguished from all other leukocytes by an unstained lobular formed nucleus which, along with the overall band size has noticeably decreased in area (volume) as compared with the prior leukocyte cells of the myeloid series. Additionally, the lobular form of the unstained nucleus becomes more bifurcated by further inward growth of the cytoplasm.

It should be noted that the metachromatic dyes may ultimately stain the cells to a point where identifications are lost. Thus, the color differences reported in this disclosure may be lost, or diminished to a great degree if analyses are not promptly performed. As practical staining occurs promptly, no extended waiting period for minimum differentials is, however, necessary.

The unique dye is prepared for the proposed end use and for the purposes of this invention in filtered aqueous solution at approximately 1% concentration of the pure basic orange 21 in distilled water. The dye concentration is not particularly critical but permits variation. It is preferred that aqueous solutions be used while fresh and that toxic additives not be included. Interference with the metachromatic reaction between dyestuff and the specific type or class or leukocyte may be totally inhibitated by the presence of any of the known classical fixatives.

The definitive language "supravital" as used herein is an important limitation. It is applied to the original blood sample and is applied to living cells freshly removed from a living organism, or one freshly sacrificed, or equivalent. As the term is used here it is intended to exclude all "fixatives" but permits use of anti-coagulants (heparin, E.D.T.A., etc.). The blood cells may also be removed from bone marrow, urine and other biological biopsy specimens containing them, including as illustrative lymphatic tissue and spleen.

Dye and blood solutions work well when combined volumetrically at a ratio of about 1:4. Gently agitate the mixture for several seconds and examine a drop of the mixture immediately as a wet mounting using a glass cover-slip under a light microscope or automated differential blood cell counting device, if available. Other means of contact between the dye and blood cell include using known media, illustratively gelatin, emulsions, etc., impregnanted with the dye at about 1% dye concentration. Fixing the sample seriously interferes with the unusual metachromatic co-action of the dyestuffs of this invention with the leukocytes.

Using basic orange 21 dye makes possible to identify and distinguish the following one from the other if they are present together: myeloblasts, promyelocytes, metamyelocytes, myelocytes, bands, neutrophils, eosinophils, basophils, B-lymphocytes, T-lymphocytes, monocytes, T-helper cells, T-suppressor cells and natural killer (NK) cells.

DETAILED DESCRIPTION OF THE INVENTION

At the time of filing herein the above-identified copending parent application, sub-populations of lymphocytes including B-cells and T-cells were not known to be identifiable by any of the prior art dyes in the field of cytology for methods of supravital blood analysis, nor were dyes known which were useful under both normal white light absorbance and fluorescent emissions to identify sub-populations of T-cells including T-helper cells and T-suppressor cells and cells known as natural killer (NK) cells.

Since the early work of the parent application, development of the art in the field of monoclonal antibody identifications, it is now possible to separate sub-population of the foregoing cells into concentrations of about 95 to 98% purity through cell sorters based upon the use of laser light stimulated fluorescent flow cell sorter cytometers. This advance in this art has made possible special antibody means for obtaining relatively pure fractions of the foregoing sub-populations of lymphocytes and other blood cells not heretofor available in high concentrations in collections of blood cells from human blood specimens.

The unusual nature of basic orange 21 dye is supravital staining of blood cells as outlined above in the above cross-referenced earlier filed applications. These applications have together suggested the ability to differentiate and identify by both absorbance and fluorescent measurement means the primary blood leukocytes and as research progressed, to differentiate further between B-lymphocytes and T-lymphocytes. The very unusual qualities of basic orange 21 have been heretofor factually established in the medical diagnostic art.

As developments in the immunology and in a fluorescence activiated cell sorting became available, it became possible to obtain relatively pure sub-populations of the T-cell and B-cell including T-helper cells and T-suppressor cells, as well as B-cells and natural killer (NK) cells through use of specific monoclonal antibodies to prepare heretofore unavailable enriched sub-populations of lymphocytes to 95–98% purity. Antibodies used for this specific sub-population concentration included anti-human immunoglobulin F(ab)$_2$ fragment for B-cells, OKT-4 for T-helper cells, OKT-8 for T-suppressor cells and Leu 7 for natural killer cells.

These enriched fractions were obtained from venous blood obtained from normal volunteers, and a Ficoll-Hypaque preparation of predominant lymphocytes were first prepared.

Using the above specific monoclonal antibodies, the high purity sub-populations of B-cells, T-helper cells, T-suppressor cells and NK cells were obtained for standardization after fluorescence activitated cell sorting had been completed.

The general practice of this invention is illustrated by the following:

A 1% solution of distilled water is made up of the selected basic quaternary cationic dye, here basic orange 21.

The aqueous solution of the selected, previously identified, single pure dye (or one can employ combination of one or more of the pure dyes as are disclosed in Tables I and II, as illustrated in Table III of the parent application) is solubilized to produce a simple aqueous dye solution. (Consideration of various volumetric proportions of the aqueous dye solution, and various strengths of aqueous dye solutions may provide optimum conditions for various specific cytological analyses.) Some experimentatin may lead to specific combinations having particular advantage and is contemplated by but beyond the scope of this disclosure.

Blood samples may be made available from various sources but fresh samples of venous blood from which erythrocytes have been removed (centrifugation, hypotonic lysis, gravity sedimentation, density gradient sedimentation, etc.) or the sample may be plasma enriched with white blood cells by known physicochemical techniques. Fixatives are avoided.

It is preferred to combine the aqueous dye and blood sample, both as freshly prepared, at the temperature of normal blood or body (about 36°–40° C.) where the analyses planned so indicates. More rapid and sharper staining at the higher temperature is generally obtained. Basic orange 21 does not appear temperature sensitive or critical.

What was originally identified as T-cells in the parent case of record above, particularly on the observation of clusters of red granules in the cytoplasm is now believed, on the basis of studies made possible by the availability of new monoclonal antibodies only recently available and developed, to identify T-suppressor cells and natural killer cells. With the present new availability of the monoclonal antibody Leu 7, the further sub-population of NK cells has been established.

Using the method outlined above and with further use of basic orange 21 as a supravital stain in conjunction with purified sub-populations of lymphocytes added to the monoclonally tagged and sorted by means of a fluorescence cell sorter, studies using a laboratory microscope capable of being use under both absorbant (white) light and fluorescent light stimulation have revealed identifying and differentiating staining patterns for each of these sub-populations of the following lymphocyte.

Referring particular to FIG. 1, which effectively summarizes the observations and findings in black and white along with descriptive language attempting to describe the living colors observed. The four classes of cells depicted are reproduced from both white light and fluorescent light stimulation of the same supravitally prepared concentrated all specimens obtained from normal blood sources.

Limitations to black and white illustration of FIG. 1 and the fact that the essential representations involve three dimensional objects and color variations which are not accurately identified by the grossness of language is an unfortunate loss of letters patent issued in black and white.

Details reported basic to and in connection with FIG. 1 were determined by means of and through the laboratory work which provided the basis for illustrative Example I.

EXAMPLE I

Highly purified populations of the various lymphocyte sub-populations were obtained by the following method:

A Ficoll-Hypaque preparation of predominantly lymphocytes was prepared from 125 ml. of heparinized venous blood from normally healthy volunteers. Various lymphocyte sub-populations were derived from aliquot portions thereof by use of specific monoclonal antibodies to obtain 95–98% purity sub-populations. These monoclonal antibodies used for sub-population determination included anti-human immunoglobulin F(ab)$_2$ for B-cell; OKT-4 for T-helper cells; OKT-8 for natural killer (NK) cells. Samples were subjected to fluorescence activated cell sorting (to obtain 95–98% purity as above) and to five drops of the so prepared lymphocyte rich suspensions after cell sorting, one drop of a 1% aqueous, filtered solution of basic orange 21 was added. Wet mounts were made and observed under both a light absorbance microscope and under a fluorescent microscope. The observations made are illustrated and summarized below and the cells are shown diagrammatically and referenced back to this description in FIG. 1 hereof. Notations made at the time where as follows:

1. The B-cells were of generally larger cell size and characterized under white light by a pale yellow nucleus and cytoplasm with no recognizable cytoplasmic inclusions. Under fluorescence, the nucleus and cytoplasm exhibited a pale blue-green fluorescence.

2. The T-helper cells were identified by being smaller lymphocytes with darker staining yellow nucleus and yellow cytoplasm. No cytoplasmic inclusions were noted. Prominent nuclear chromatin aggregates were noted in the nucleus. Under fluorescence, a somewhat deeper blue-green fluorescence, brighter than in the case of the B-cells was noted for the nucleus and cytoplasm, the cytoplasm being somewhat less opaque.

3. The T-suppressor cells were also smaller than the B-cells, very similar in color of nucleus and cytoplasm to the T-helper cells and containing prominent nucleus chromatin aggregates. Prominent differences observed over the T-helper cells were a plurality of from 2 to 6 small, bright red, granules in the lighter yellow cytoplasm. Under fluorescence, the nucleus and cytoplasm differed only in that the plurality of small granules present fluoresced yellow.

4. The natural killer cells (NK) were unusually larger cells having a dark yellow nucleus possibly as large or larger than the nucleus of the B-cell, T-helper and T-suppressor cells including both nucleus and cytoplasm containing similar chromatin aggregates in the larger yellow nucleus. The cytoplasm was also yellow of commensurate total area to the nucleus, but characterized by a greater plurality of larger, red granules (from about 4 to 20) in the larger area cytoplasm when observed under white light. Under fluorescence, the cytoplasm and nucleus both fluoresced similarly in a pale blue-green, and the large granules in the cytoplasm were a bright fluorescent yellow.

The information observed and reported in the Example and FIGURE summarizes the advance in the art herein disclosed. Briefly, by examination of a single aliquot specimen of human blood from a donor as shown in the Example and as summarized in the FIGURE under either white light or fluorescent or both one can identify, distinguish and enumerate the sub-populations of lymphocytes as shown and/or determine ratios of said cells present. Only one dye is essential. No time delay is required. Costly monoclonal antibodies and complex cytochemistry is not required.

DEVELOPMENT OF THE INVENTION

In the foregoing specification and examples there has been some emphasis on the importance of the advances here disclosed in application to automated differential leukocyte computing devices. There is no known "off the shelf" equipment capable presently without some modification of taking advantage of the method herein disclosed which has been employed manually. Those skilled in the art and working in the field of medical technology are aware of the importance of rapid, accurate determination of the various differential leukocyte counts for a variety of ends. It has been estimated that in the United States each day an half million differential leukocyte counts are performed, most of them by manual techniques at an annual cost of over 750 million dollars.

Such counts, whether manual or automated, have a fundamental requirement of identification, spectral differentiation, enumeration and diagnostic aid in practice of medicine. The foregoing advance in these fundamentals will no doubt give rise in advances in ancillary automated equipment as herein indicated.

Blood counts as are of concern herein, whether manually or automated, are vital aids in examination and determination of the nature of disease. Fevers of unexplained origin; whether viral or non-pyrogenic infection, pyrogenic involving appendix, gall-bladder, fallopian tubes; prognosis of patients with various diseases in various stages; malignancies including Hodgkin disease; plumonary disease; surveillance of patient treatment with adrenocortical steroids; various kinds of acute and chronic leukemias; differentiation in diagnosis between aseptic infection of bone and osteomyelitis; bacterial infections and many other medical questions are aided in diagnosis, prognosis and treatment by accurate leukocyte counting, analysis and cytological study.

Having described the best mode presently known to practice the invention herein disclosed, what is claimed is:

1. A method of qualitative and quantitative analysis of a human blood specimen under supravital conditions to determine subpopulatins of lymphphocytes consisting essentially of B-cells, T-helper cells, T-suppressor cells, and Natural Killer (NK) cells which comprises staining a fixative-free specimen with an aqueous solution of not more than about 1% of the cationic dye Basic Orange #21, differentiating, identifying and enumerating said subpopulations by comparison of the size, shape, color and component differentials observable within the individual nucleus and cytoplasm of each cell of said subpopulations including the presence or absence of and the relative size, number and characteristic color of granules observable in the cytoplasm and the characteristic color differentials among said subpopulations in their respective nuclei by exposing the dyed specimen to illumination by at least one of white light and fluorescent light.

2. The method of claim 1 wherein the illumination is white light.

3. The method of claim 1 wherein the illumination is fluorescent light.

4. The method of claim 1 wherein the illumination is white light and fluorescent light.

5. The method of claim 1 further including staining known lymphocytes corresponding to said subpopulations with said aqueous dye solution, exposing the stained known lymphocytes to white light and fluorescent light emissions thereby to establish a standard cell outline detail classification for comparison purpose with an unknown cell population of lymphocytes in a human blood specimen.

* * * * *